United States Patent
Takahashi et al.

(10) Patent No.: US 12,408,863 B2
(45) Date of Patent: Sep. 9, 2025

(54) SPINAL ALIGNMENT-ESTIMATING APPARATUS, SYSTEM FOR ESTIMATING SPINAL ALIGNMENT, METHOD FOR ESTIMATING SPINAL ALIGNMENT, AND NON-TRANSITORY COMPUTER-READABLE RECORDING MEDIUM HAVING STORED THEREIN PROGRAM FOR ESTIMATING SPINAL ALIGNMENT

(71) Applicant: TOHOKU UNIVERSITY, Sendai (JP)

(72) Inventors: Yusei Takahashi, Sendai (JP); Ko Hashimoto, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 825 days.

(21) Appl. No.: 17/673,878

(22) Filed: Feb. 17, 2022

(65) Prior Publication Data
US 2022/0265205 A1 Aug. 25, 2022

Related U.S. Application Data

(63) Continuation of application No. PCT/JP2021/006490, filed on Feb. 19, 2021.

(51) Int. Cl.
- *A61B 5/00* (2006.01)
- *G06T 7/00* (2017.01)
- *G06T 7/70* (2017.01)

(52) U.S. Cl.
CPC .......... *A61B 5/4566* (2013.01); *G06T 7/0012* (2013.01); *G06T 7/70* (2017.01); *G06T 2207/30012* (2013.01)

(58) Field of Classification Search
CPC  A61B 5/4561–4566; A61B 5/68–6803; G06T 7/0012–0016; G06T 7/70–77; G06T 2207/30012
See application file for complete search history.

(56) References Cited

U.S. PATENT DOCUMENTS

| | | | |
|---|---|---|---|
| 10,839,481 B1 * | 11/2020 | Chen | G06T 7/344 |
| 2002/0169376 A1 | 11/2002 | Pettibon | |
| 2014/0127658 A1 | 5/2014 | Rekimoto | |

(Continued)

FOREIGN PATENT DOCUMENTS

| | | |
|---|---|---|
| CN | 103479361 A | 1/2014 |
| CN | 103945763 A | 7/2014 |

(Continued)

OTHER PUBLICATIONS

The European Search Report with Supplementary European Search Report and the European Search Opinion issued by the European Patent Office for corresponding European Patent Application No. 21 854 854.3, dated Aug. 30, 2024.

(Continued)

*Primary Examiner* — Matthew Kremer
*Assistant Examiner* — Aaron Merriam
(74) *Attorney, Agent, or Firm* — Myers Wolin, LLC

(57) ABSTRACT

A spinal alignment estimating apparatus 1 includes a memory, and a processor coupled to the memory, the processor being configured to obtain a position of a head of a user measured in relation to a viewing target, and an angle of the head of the user, and estimate a spinal alignment of the user based on the position and the angle.

9 Claims, 11 Drawing Sheets

(56) References Cited

U.S. PATENT DOCUMENTS

| | | | |
|---|---|---|---|
| 2016/0140826 A1* | 5/2016 | Sahiholnasab | A61B 5/1121 600/587 |
| 2019/0038215 A1* | 2/2019 | Cunico | A61B 5/7278 |
| 2019/0313967 A1 | 10/2019 | Lee | |
| 2020/0060582 A1* | 2/2020 | Nakamura | A61B 5/1121 |
| 2020/0069243 A1 | 3/2020 | Matsumoto et al. | |

FOREIGN PATENT DOCUMENTS

| | | |
|---|---|---|
| JP | 2014-90841 A | 5/2014 |
| JP | 2015-39472 A | 3/2015 |
| JP | 2015-107141 A | 6/2015 |
| JP | 2020-54433 A | 4/2020 |
| JP | 2020-74876 A | 5/2020 |
| WO | 2013/152607 A1 | 10/2013 |
| WO | 2016/079585 A1 | 5/2016 |
| WO | 2017/141958 A1 | 8/2017 |

OTHER PUBLICATIONS

Hosub et al., "Mobile Posture Monitoring System to Prevent Physical Health Risk of Smartphone Users", Low Power Electronics and Design, Sep. 5, 2012, pp. 592-593, XP059221647, cited in the EESR.

Hobeom et al., "Novel Wearable Monitoring System of Forward Head Posture Assisted by Magnet-Magnetometer Pair and Machine Learning", IEEE Sensors Journal, IEEE, Dec. 16, 2019, pp. 3838-3848, vol. 20, No. 7, USA, XP011776944, cited in the EESR.

Notice of Reasons for Refusal issued by the Japan Patent Office for corresponding Japanese Patent Application No. 2021-536242, mailed Oct. 12, 2021, with an English translation.

International Search Report and Written Opinion of the International Searching Authority issued by Japan Patent Office for corresponding International Patent Application PCT/JP2021/006490, dated May 11, 2021, with an English translation.

Kato et al., "Effect of Posture Feedback Band on Posture Alignment and Pain during a Visual Display Terminal Task", Journal of the Japanese Society for Experimental Mechanics, Dec. 2016, vol. 16, No. 4, pp. 315-319.

Communication pursuant to Article 94(3) EPC issued by the European Patent Office for corresponding European Patent Application No. 21854854.3, mailed on Feb. 12, 2025.

* cited by examiner

FIG.9

TABLE OF RESULT OF MULTIPLE REGRESSION ANALYSIS
ATTRIBUTE GENDER: MALE, AGE: TWENTIES, BODY FIGURE: SLENDER SHAPE

| | C2-C7 VERTICAL ANGLE | T1 slope | C7-T3-T8 | T3-T8-T12 | T12-L3-S |
|---|---|---|---|---|---|
| MULTIPLE CORRELATION COEFFICIENT R | 0.972 | 0.996 | 0.868 | 0.849 | 0.735 |
| MULTIPLE COEFFICIENT OF DETERMINATION $R^2$ | 0.945 | 0.991 | 0.753 | 0.721 | 0.541 |
| INTERCEPT $A_5$ | 32.1 | 78.6 | 133.8 | 164.2 | 180.4 |
| COEFFICIENT $A_1$ OF TERM OF HEAD SLOPE ANGLE $\Theta_S$ | 0.411 | -0.159 | 0.542 | -0.021 | -0.024 |
| COEFFICIENT $A_2$ OF TERM OF VIEWING DISTANCE d | 0.002 | -0.034 | 0.037 | -0.025 | -0.022 |
| COEFFICIENT $A_3$ OF TERM OF SQUARE OF HEAD SLOPE ANGLE $\Theta_S$ | -0.00107 | 0.00301 | -0.00375 | -0.00060 | 0.000115 |
| COEFFICIENT $A_4$ OF TERM OF SQUARE OF VIEWING DISTANCE d | -0.0000328 | -0.0000361 | 0.0000015 | 0.0000131 | 0.0000102 |

SPINAL ALIGNMENT-ESTIMATING APPARATUS, SYSTEM FOR ESTIMATING SPINAL ALIGNMENT, METHOD FOR ESTIMATING SPINAL ALIGNMENT, AND NON-TRANSITORY COMPUTER-READABLE RECORDING MEDIUM HAVING STORED THEREIN PROGRAM FOR ESTIMATING SPINAL ALIGNMENT

CROSS-REFERENCE TO RELATED APPLICATION

This application is a continuation application of International Patent application No. PCT/JP2021/006490, filed on Feb. 19, 2021, and designated the U.S., the entire contents of which are incorporated herein by reference.

FIELD

The embodiment(s) discussed herein is(are) related to a spinal alignment-estimating apparatus, a system for estimating a spinal alignment, a method for estimating a spinal alignment, and a computer-readable recording medium having stored therein a program for estimating a spinal alignment.

BACKGROUND

With the widespread use of Visual Display Terminals (VDT) such as computer displays, problems of mental and physical symptoms (VDT syndromes) caused by long VDT operations have been regarded have arisen.

In particular, when using a portable VDT such as a laptop computer or a smart phone, users tend to lean forward. Persistent forward-leaning posture places a load on the muscles surrounding the cervical spine that supports the weight of the head and causes various symptoms such as stiff neck and headache.

A wearable device that can be put or worn on the body and a terminal device that can be incorporated into the VDT itself when being used have been known as examples of a device that monitors the position in the anteroposterior direction of the head-and-neck of the subject using the VDT over time and determines whether the user is in a bad posture and alert the subject.

As an example of the wearable-type device, a lensless frame having an inclination sensor measures the slope angle in the front-rear direction of the frame with respect to the horizontal axis (viewing angle 0°), and alerts the user when the slope angle is outside a predetermined tolerance range (see Patent Document 1).

As another example of the wearable-type device, smart eyeglasses provided with multiple sensors alerts the user when the slope angle and the pitch angle in the anteroposterior direction of the head of the user measured by an inertial sensor exceed respective predetermined tolerance values, or the distance to the target measured by a distance sensor is less than the set value for a given time period or longer (see Patent Document 2).

On the other hand, as an example of the terminal-type device, a mobile terminal incorporating therein multiple sensors calculates the angle in the front-rear direction in the space of the mobile terminal with an acceleration sensor, measures the distance between the screen and the user's eyes with a distance sensor, determines the user's posture from these two pieces of information, and alerts the user (see Patent Document 3).

Patent Document 1: WO 2016/079585
Patent Document 2: Chinese Patent Publication No. 103479361
Patent Document 3: Japanese Laid-open Patent publication No. 2015-39472

In each of the above methods of determining a posture focuses only on the head-and-neck of a subject, and determines the posture based on whether or not the slope angle of the head-and-neck in the anteroposterior direction and the distance between the head-and-neck and VDT are within the tolerance ranges. However, a postural change, particularly in the sitting posture, involves not only the head-and-neck, but also all of positions of the cervical spine, the thoracic spine, the lumbar spine, and the pelvis that constituting the spine (see FIGS. 1 and 2). Therefore, there is a possibility that the posture of the subject is not accurately estimated by the posture determination based only on the information on the head-and-neck.

Usually, information of arrangement of spine (spinal alignment) of a human is obtained from a three-dimensional motion analyzer such as a motion capture or from X-ray imaging. However, the motion analyzer requires an expensive large-scale apparatus, and therefore has difficulty to use on a daily basis for everyone. X-ray imaging involves radiation exposure and is usually not acceptable unless there are justifiable medical reasons. In addition, it is impossible to dynamically obtain the posture of the subject using a VDT over time.

In one aspect, the object of the techniques described herein are directed to estimate a spinal alignment of a subject person in a sitting posture over time, dynamically, and accurately with a simple device.

SUMMARY

In one aspect, a spinal alignment estimating apparatus includes: a memory; and a processor coupled to the memory, the processor being configured to: obtain a position of a head of a user measured in relation to a viewing target and an angle of the head of the user; and estimate a spinal alignment of the user based on the position and the angle.

In one aspect, the spinal alignment of a user in a sitting posture can be estimated over time, dynamically, and accurately with a simple device.

BRIEF DESCRIPTION OF DRAWINGS

FIG. 9 is a diagram showing an example of a result of multiple regression analysis using coefficients being related to alignment of each part of the spine and being obtained by using data obtained by an apparatus and a result of measuring with a three-dimensional motion analyzer;

DESCRIPTION OF EMBODIMENT(S)

Figure 1:
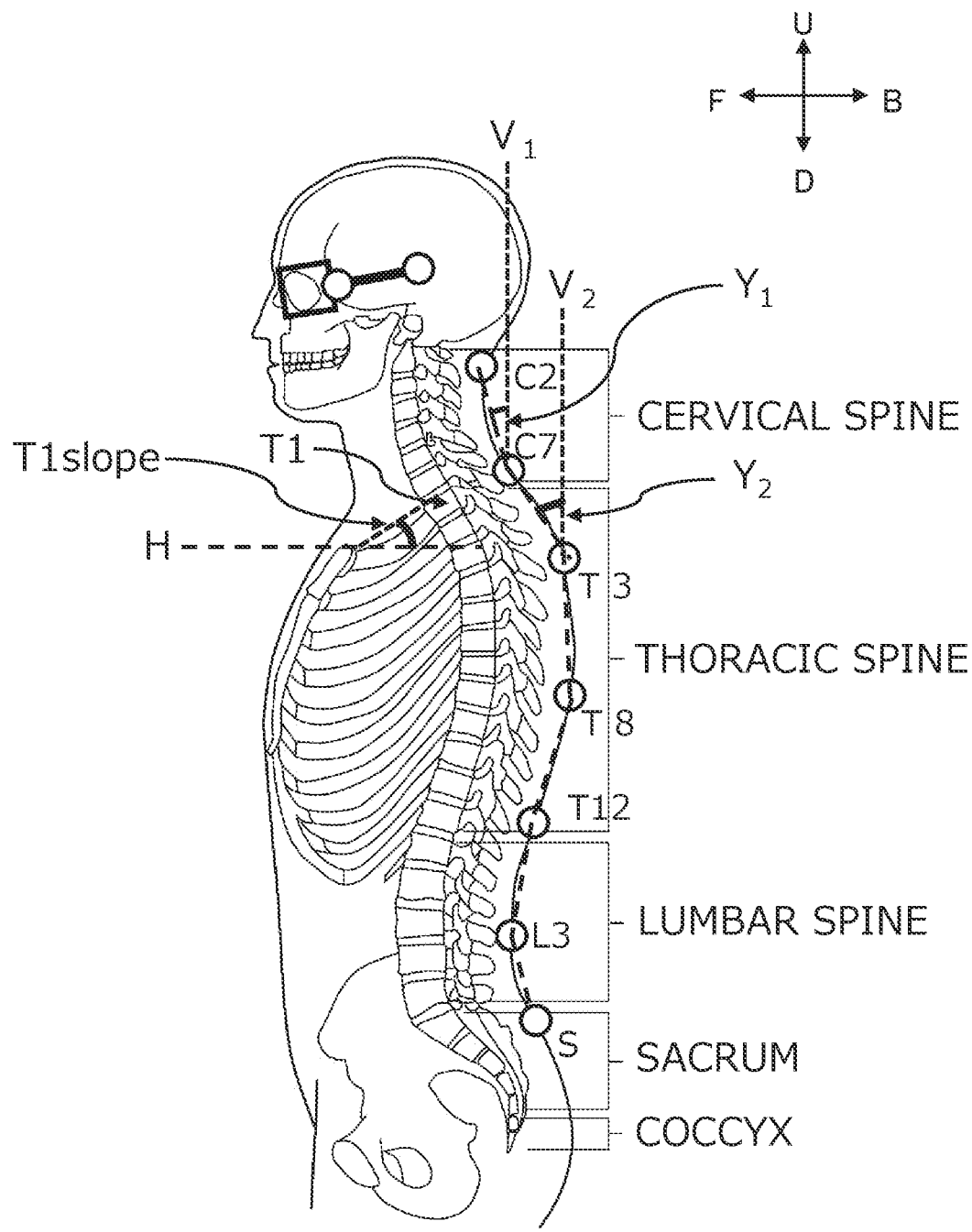
FIG. 1 is a diagram illustrating an index used for estimating a spinal alignment of a user.

Hereinafter, an embodiment of the present disclosure will now be described with reference to the accompanying drawings. However, the embodiment described below is merely illustrative and the present embodiment can be variously modified and implemented without departing from the scope thereof. In the drawings to be used in the following description, like reference numbers denote the same or similar parts, unless otherwise specified.

In the embodiment, the directions used in the description are defined as follows. The horizontal direction will be described in detail in the front-rear direction (the front is indicated by "F" and the rear is indicated by "B" in the drawings) and in the left-right direction (the left is indicated by "L" and the right is indicated by "R" in the drawings). The left and right directions are determined on the basis of a state directing from the rear to the front. In addition, the direction that the gravity acts among the vertical direction is downward (indicated by "D" in the drawings) and the opposite direction of the downward is defined as upward (indicated by "U" in the drawings).

[1] One Embodiment

[1-1] Definition of the Human Spine

Here, the terms related to the human spine and the reference symbols for illustrative purposes of the present application will now be defined.

Figure 2:
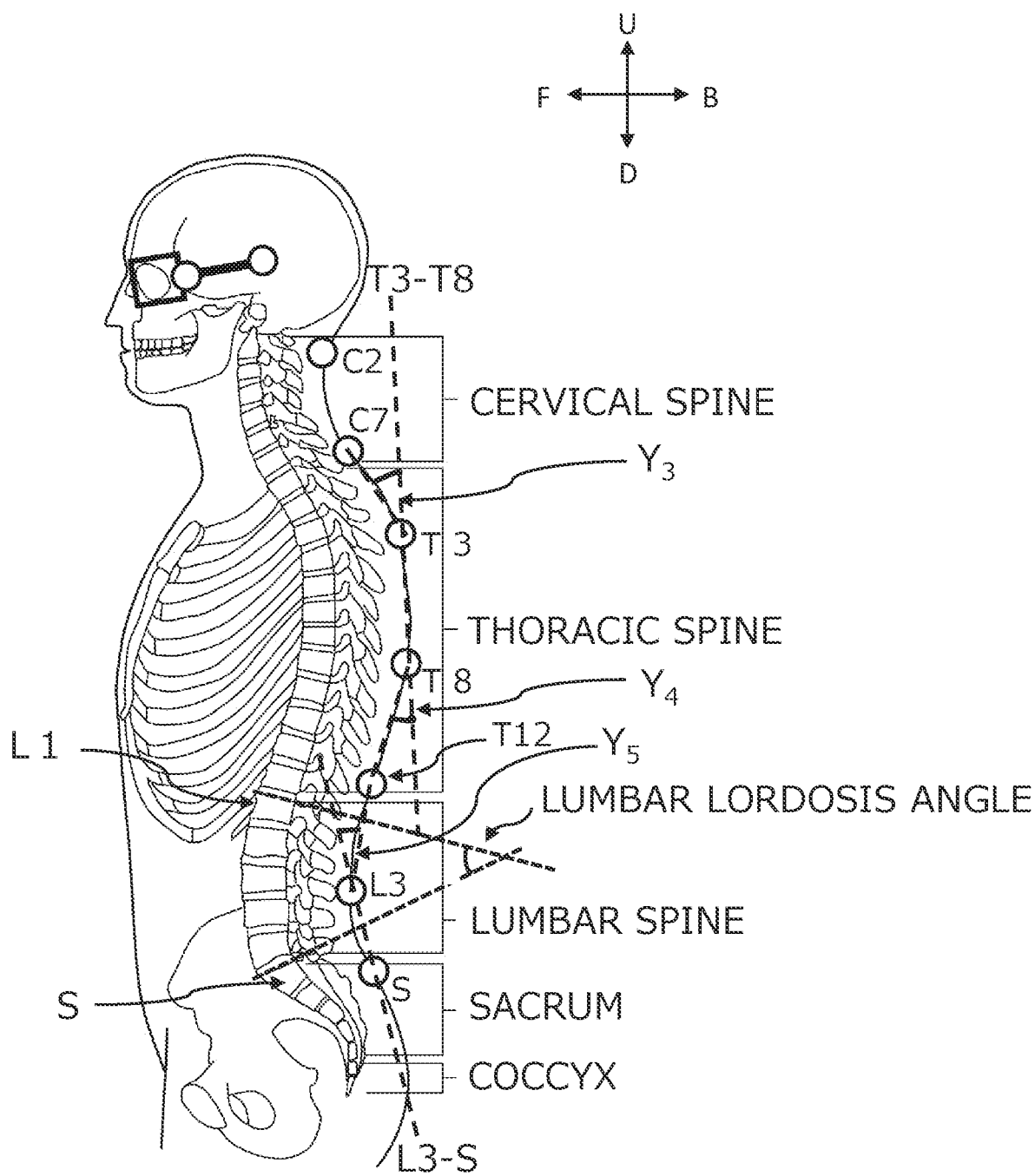
FIG. 2 is a diagram illustrating an index used for estimating a spinal alignment of a user.

FIGS. 1 and 2 are diagrams each illustrating an index used for estimating a spinal alignment of a human. The human spine is composed of the cervical spine, the thoracic spine, the lumbar spine, the sacrum, and the coccyx, and the arrangement of these bones is referred to as the spinal alignment. Bones are abbreviated from English-language acronyms, i.e., the cervical spine is represented by C1-C7; the thoracic spine is represented by T1-T12; the lumbar spine is represented by L1-L5; the sacrum is represented by S; and the coccyx is represented by Co. In the technique described in this specification, for estimating the posture of the user operating a VDT in the sitting posture uses the body surface median at the heights corresponding to the second cervical spine C2, the seventh cervical spine C7, the third thoracic spine T3, the eighth thoracic spine T8, the twelfth thoracic spine T12, the third lumbar spine L3, and the sacrum S is used as the reference points. The white circles (markers) arranged in FIGS. 1 and 2 indicate the position of the body surface corresponding to the positions of the bones related to the posture of the user in the sitting posture.

As described above, connecting the centers of the white circles arranged on the body surface corresponding to the median of C2, C7, T3, T8, T12, L3, and S, which are the reference points for estimating the posture of the user in the sitting posture, by a straight line obtains one polygonal line drawn along the back surface of the user. The polygonal line is a line that roughly indicates the spinal alignment in the anteroposterior direction of the user. The angles that lines connecting points form in conjunction with the horizontal line and vertical line and the angles formed by the two adjacent lines approximate the degrees of the slopes and curvature of the respective parts of the spine.

The angles in this section are angles in the anteroposterior (sagittal) direction of the spinal column. In FIG. 1, the angle (C2-C7 vertical angle) formed by the line segment connecting the C2 and the C7 and the vertical line $V_1$ is represented by $Y_1$. The angle $Y_1$ is the angle representing the degree of leaning forward of the cervical spine. In FIG. 1, the angle formed by a line segment connecting the C7 and the T3 and the vertical line $V_2$ is represented by $Y_2$. The angle $Y_2$ approximates the T1 slope that is a key indicator to determine the cervical spinal alignment, which corresponds to the angle that the upper surface of the first thoracic vertebral body (T1) forms in conjunction with the horizontal line H shown in FIG. 1. The T1 slope indicates how many degrees the upper surface of the vertebral body of the first thoracic spine is inclined with respect to the horizontal plane, and is clinically one of the indices that defines the cervical spinal alignment.

In FIG. 2, a sharp angle formed by a line segment connecting the C7 and the T3 and a line segment obtained by extending upward a line segment connecting the T3 and the T8 is represented by $Y_3$. The angle $Y_3$ approximates the kyphosis of the upper thoracic spine, which corresponds to the curvature of the posterior-convex spine of the upper thoracic spine (the upper thoracic kyphosis angle). In FIG. 2, a sharp angle formed by a line segment obtained by extending downward a line segment connecting the T3 and the T8 and the line segment connecting the T8 and the T12 is represented by $Y_4$. The angle $Y_4$ approximates the kyphosis of the middle-to-lower thoracic spine, which corresponds to the curvature of the posterior-convex spine in the middle to the lower portion of the thoracic spine (middle-to-lower thoracic kyphosis angle). In FIG. 2, a sharp angle formed by a line segment connecting the T12 and the L3 and a line segment obtained by extending upward a line segment connecting the L3 and the S is represented by $Y_5$. The angle $Y_5$ approximates the lordosis of the lumbar spine, which corresponds to the curvature of the anterior-convex spine in the lumbar spine region (lumbar lordosis angle). The lumbar lordosis angle is generally indicated by the angle formed by the upper surface of the L1 spine body and the extension line of the upper surface of the sacrum S as shown in FIG. 2, and is an index related to the lumbar alignment.

The cervical forward slope angle, the T1 slope, the upper thoracic kyphosis angle, the middle-to-lower thoracic kyphosis angle, and the lumbar lordosis angle, which are indices of the spinal alignment described above, are values originally measured by radiography. The angles $Y_1$ to $Y_5$ are estimated approximate values based on the reference points of the body surface, which are originally not known unless being subjected to radiography.

[1-2] Description of One Embodiment

The viewing target in the present disclosure includes all objects as long as the distance between the object and the user can be measured, such as a display screen of a television or the like, a visual display terminal of a computer display or an operating screen of a mobile device or the like, as well as books and pictures. However, the distance between the viewing target and the user is preferably within a range of about 5 meters, which affects the inclination of the head of the user. In the following description, the viewing target is exemplified by an operating screen of an operation terminal such as a computer display.

Figure 3:
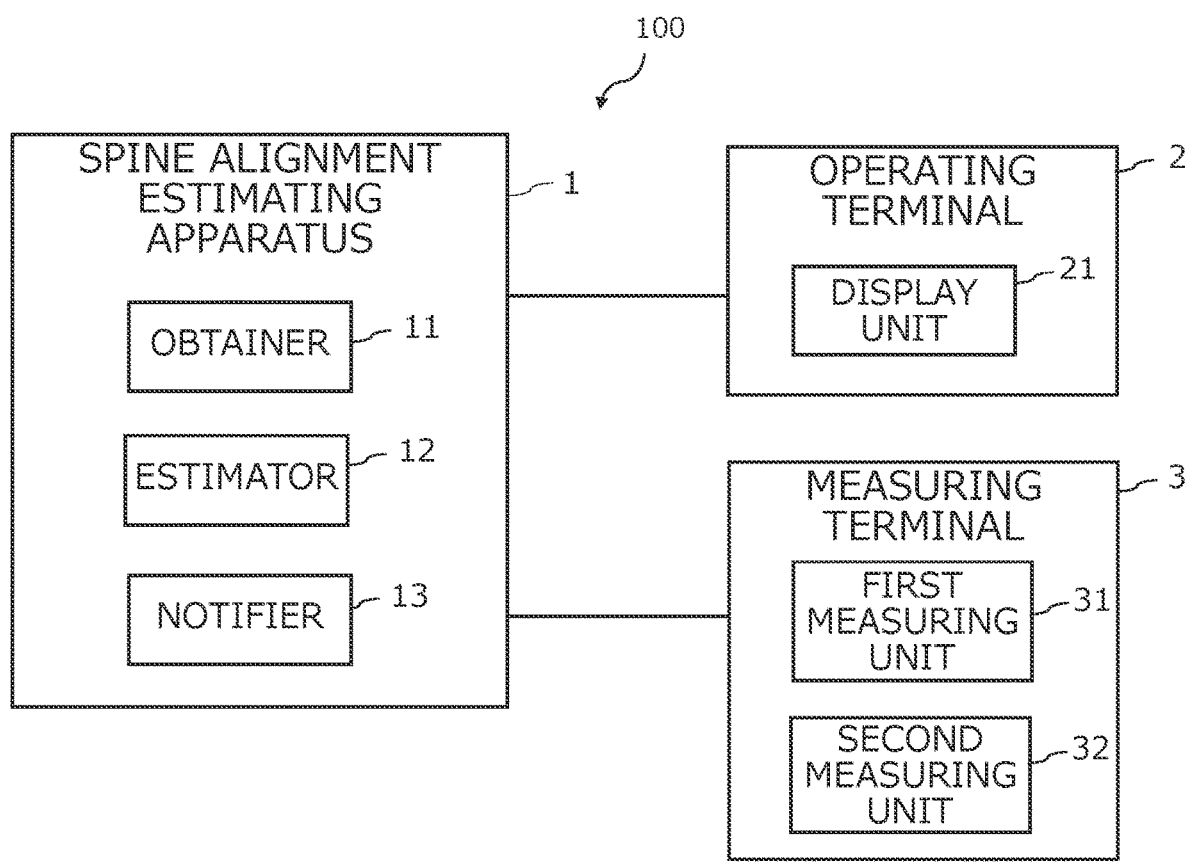
FIG. 3 is a diagram illustrating a system for estimating a spinal alignment according to an embodiment.

FIG. 3 is a diagram illustrating a spinal alignment estimating system 100 according to an embodiment. As shown in FIG. 3, the spinal alignment estimating system 100 may illustratively include a spinal alignment estimating apparatus 1, an operating terminal 2, and a measuring terminal 3.

The spinal alignment estimating system 100 is a system for estimating the spinal alignment of a user, and is an example of an information processing system.

The spinal alignment estimating apparatus 1, the operating terminal 2, and the measuring terminal 3 may be connected to each other via a network. FIG. 3 shows an example of wired connection, but these elements may be wirelessly connected.

The operating terminal 2 is an example of an information processing terminal operated by a user (in other words, a subject person). Examples of the operating terminal 2 include various computers such as a Personal Computer (PC) and a smart phone.

As shown in FIG. 3, the operating terminal 2 may include a display unit 21 that displays information on an operating screen (viewing target). The display unit 21 presents various kinds of information to the user through the operating screen. The presented information may include the position of the head of the user measured by a first measuring unit 31 that is to be descried below, the angle of the head of the user measured by a second measuring unit 32, and information output from a notifier 13 of the spinal alignment estimating apparatus 1 which are described below.

The measuring terminal 3 is an example of an instrument unit that measures various data in a state of being worn by a user. For example, the measuring terminal 3 may be wearable (detachable) to a user's wearing object such as eyeglasses, a headband, a necklace, an earphone, or the like worn by the user, or may be integrated (undetachable) with the wearing object of the user.

As shown in FIG. 3, the measuring terminal 3 may include the first measuring unit 31 and the second measuring unit 32. The first measuring unit 31 measures the position of the head of the user in relation to the operating screen of the operating terminal 2. In other words, the first measuring unit 31 measures the distance between the operating screen of the operating terminal 2 and the user in front of the operating screen. Alternatively, the first measuring unit 31 may measure, as the distance, a change from the initial position, which is the position of the head of the user at starting.

The second measuring unit 32 measures the angle of the head of the user. In other words, the second measuring unit 32 measures the slope angle of the head of the user facing the operating screen of the operating terminal 2. If the operating terminal 2 is a personal computer, since the angle of the operating screen is substantially constant, the angle of the head of the user can be interpreted as the angle in relation to the screen.

The measuring terminal 3 transmits the position of the head of the user measured by the first measuring unit 31 and the angle of the head of the user measured by the second measuring unit 32 to the spinal alignment estimating apparatus 1.

The spinal alignment estimating apparatus 1 is an example of a data analysis apparatus, an information processing apparatus, or a computer that analyzes data, generates display information, and manages files.

As shown in FIG. 3, the spinal alignment estimating apparatus 1 may include an obtainer 11, an estimator 12, and the notifier 13. The obtainer 11 obtains the position of the head of the user measured by the first measuring unit 31 and the angle of the head of the user measured by the second measuring unit 32 from the measuring terminal 3. The estimator 12 estimates the spinal alignment of the user based on the position and the angle of the head of the user obtained by the obtainer 11. The notifying unit 13 notifies the user of possible abnormality of the posture on the basis of the result of the estimation by the estimator 12.

[1-3] Example of Appearance Structure of Measuring Terminal

Figure 4:
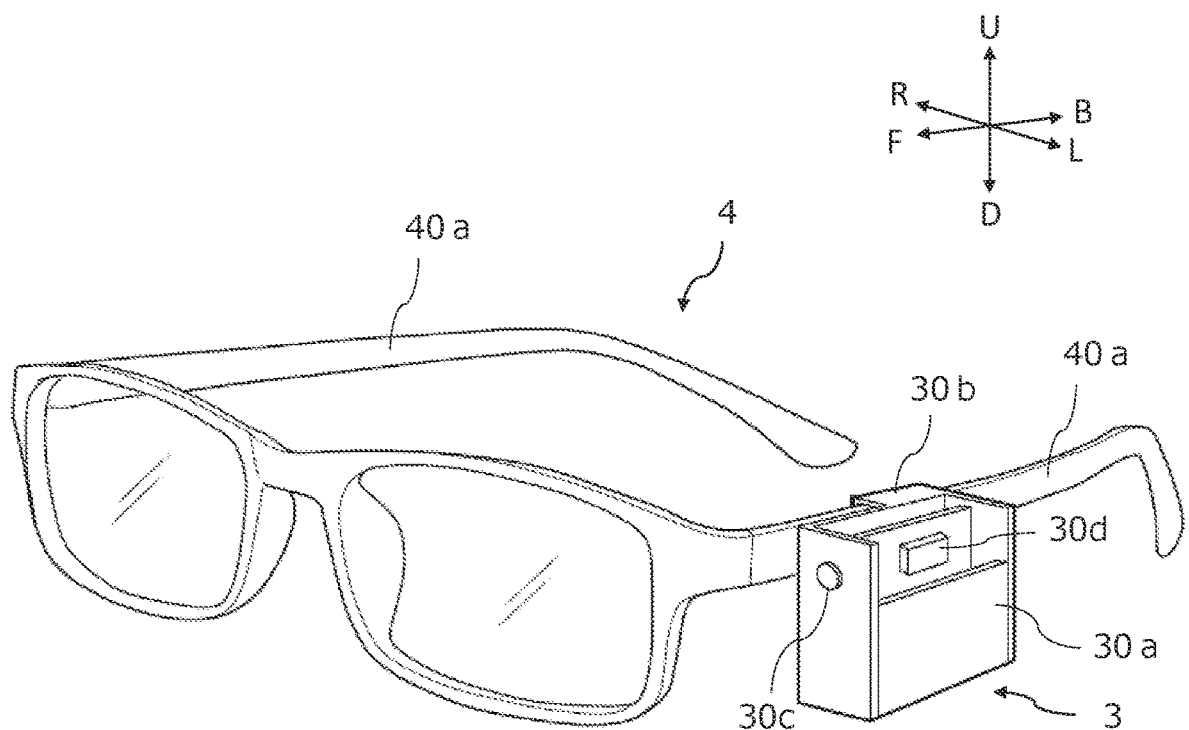
FIG. 4 is a diagram illustrating an appearance structure of a measuring terminal of one embodiment attached to eyeglasses.

FIG. 4 is a diagram illustrating an appearance structure of the measuring terminal 3 of one embodiment. Here, the measuring terminal 3 which can be mounted on eyeglasses will be described as an example. The measuring terminal 3 is mounted on a temple 40a of eyeglasses 4 of an ordinary shape used in daily life. The measuring terminal 3 has a casing 30a, which is provided with a hook 30b for mounting on the temple 40a. Here, the casing 30a is attached to the outside (left side) of the temple 40a on the left side of the eyeglasses 4. The position of the measuring terminal 3 on the temple 40a is preferably around the user's temple, which is a position close to the eye of the user wearing the eyeglasses 4.

In the casing 30a, a position measuring device 30c and an angle measuring device 30d are accommodated. The position measuring device 30c is an example of a device that measures the position of the head of the user in relation to the operating screen of the operating terminal 2. In other words, the position measuring device 30c is an example of the first measuring unit 31. Examples of the position measuring device 30c are optical, radio, or ultrasonic distance measuring sensor or the like. Here, an example in which the camera 30c is used as the position measuring device 30c will be described.

The angle measuring device 30d is an example of a device that measures the angle of the head of the user in relation to the operating screen of the operating terminal 2. In other words, the angle measuring device 30d is an example of the second measuring unit 32. An example of the angle measuring device 30d includes an inertial sensor or a slope sensor including an acceleration sensor and a gyro. Here, the angle measuring device 30d uses an acceleration sensor 30d will be described as an example.

[1-4] Description of Estimator

Next, description will now be made in relation to an example of a process of the estimator 12 of the spinal alignment estimating apparatus 1 described above along with an example of the spinal alignment estimating system 100 using the measuring terminal 3 that can be mounted on the eyeglasses 4 and the notebook PC 2 as the operating terminal 2.

Figure 5:
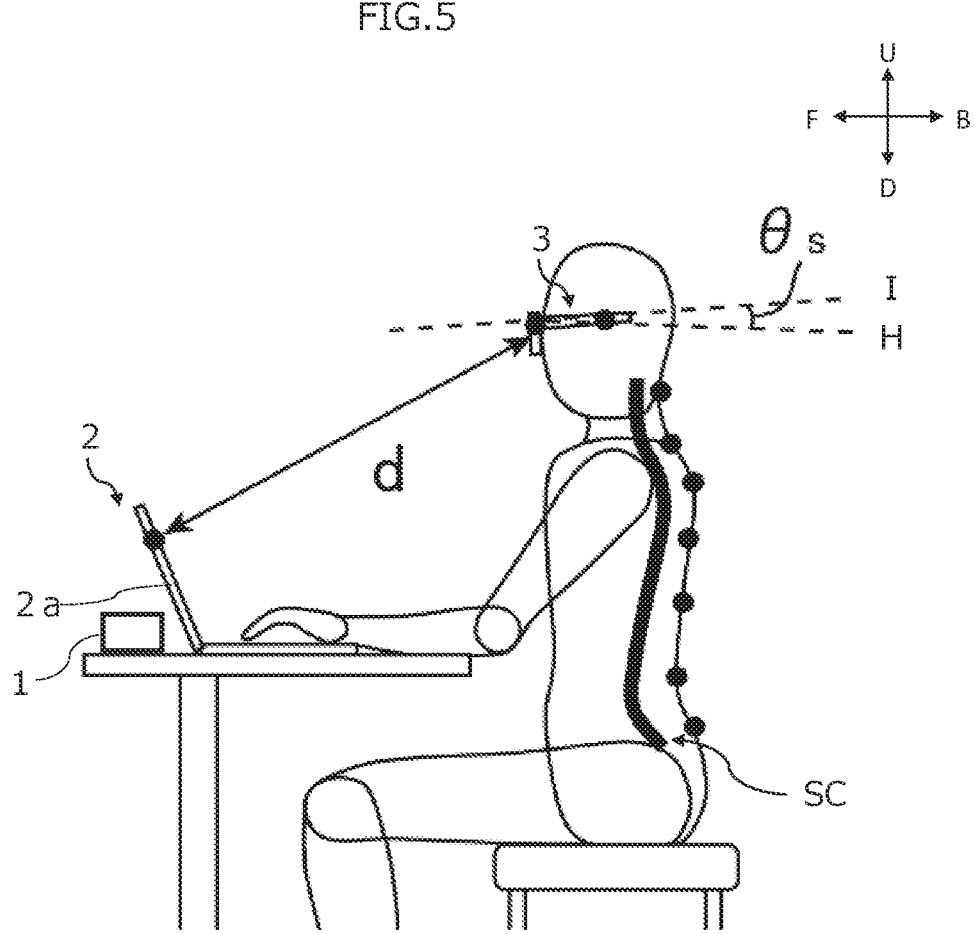
FIG. 5 is a diagram illustrating a distance between the head of a user and a VDT and an angle of the head of the user.

FIG. 5 is a diagram illustrating the distance between the head of the user and the VDT and the angle of the head of the user. As shown in FIG. 5, in the present embodiment as an optimum example, a case where the user wears the eyeglasses 4 attached with the measuring terminal 3 and operates the notebook PC 2 in a sitting posture will be described. The line extending along the posterior side (back surface) of the user's body indicates the spine SC. Further, black circles placed on the back surface of the user along the spine SC represent the position of the skin surface corresponding to the position of the bones related to the posture of the user in the sitting posture, and coincide with the position of the white circles in FIGS. 1 and 2.

The camera (position measuring device 30c) of the measuring terminal 3 measures the position of the head of the user in relation to the operating screen 2a, in other words, the distance d between the operating screen 2a of the notebook PC (operating terminal) 2 and the head of the user. Since the measuring terminal 3 is attached at a position near to the temple of the user, it can be said that the distance d measured by the camera 30c is the viewing distance d from the eyes of the user to the operating screen 2a.

The acceleration sensor 30d of the measuring terminal 3 measures the angle $\theta_S$ of the head of the user. The angle $\theta_S$ is the slope relative to the user's head, i.e., an inclination of the line connecting the eye and the upper aural edge with respect to the baseline (e.g., a horizontal line). When the position of the temple 40a in the front posture is indicated by a horizontal line H and the position of the temple 40a in the inclined posture is indicated by a virtual line I, it can be said that the angle $\theta_S$ is an angle between the horizontal line H and the virtual line I.

The estimator 12 estimates the spinal alignment of the user by calculating the angles formed by given parts constituting the spinal alignment using the coefficients $A_1$ to $A_5$ stored in the storing device 10c (described below with reference to FIG. 11) of the estimator 12 to be described below on the basis of the position (viewing distance d) and the angle (slope angle $\theta_S$) of the head of the user obtain by the obtainer 11.

Hereafter, description will be made in relation to the correlations among the spinal alignment, the viewing distance d, and the slope angle $\theta_S$ obtained by experiments.
(Experiment to Examine the Correlation Between the Measured Value of the Motion Analyzer and the Measured Value of the Measuring Terminal 3)

Figure 6A:
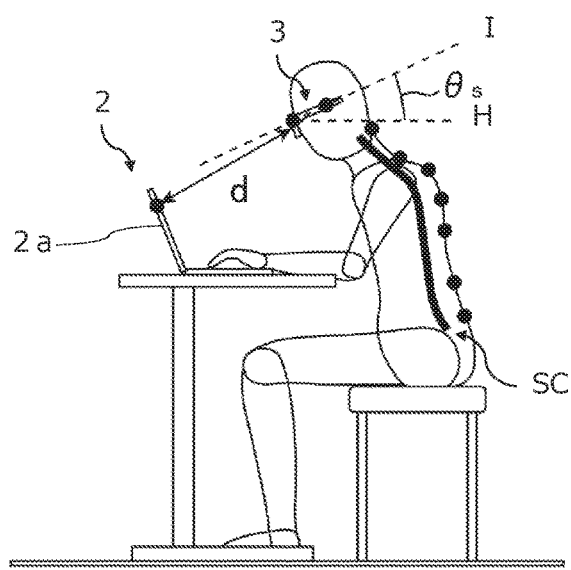
FIG. 6A and FIG. 6B are diagrams illustrating fluctuation of the spinal alignment of the user in a sitting posture.
Figure 6B:
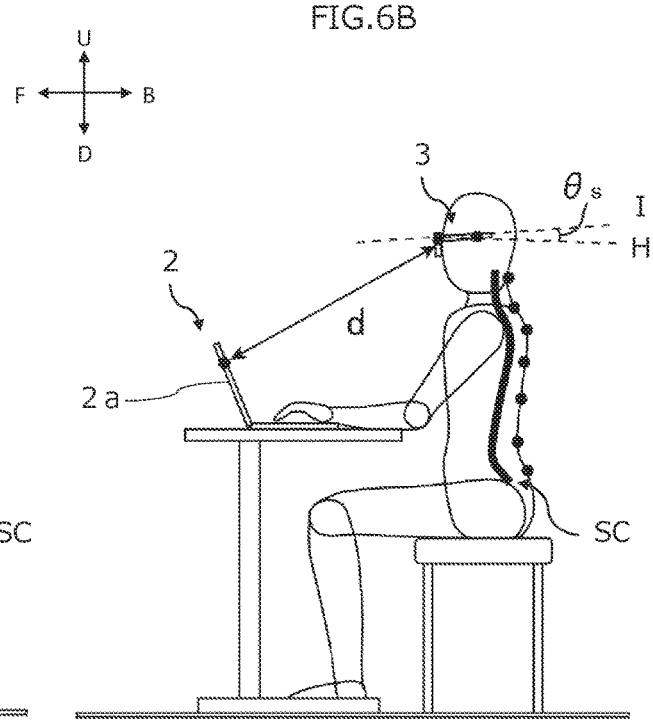

FIG. 6A and FIG. 6B are diagrams illustrating fluctuation of the spinal alignment of the user in a sitting posture. An experiments was performed under predetermined conditions to examine correlations among the spinal alignment, the viewing distance d, and slope angle $\theta_S$. More specifically, the spatial coordinate of the spine index was obtained with a three-dimensional motion analyzer using infrared-type high-speed cameras placed at eight locations in all directions, and simultaneously, the head slope angle $\theta_S$ and the viewing distance d were obtained with the measuring terminal 3. The three-dimensional motion analyzer obtained coordinate information at a spatial resolution of 1 mm and a sampling rate of 120 Hz. The measuring terminal 3 obtained the head slope angle $\theta_S$ and the viewing distance d at a sampling rate of 10 Hz. The experiment was performed on multiple subjects.

The subject wore the eyeglasses 4 attached with the measuring terminal 3. At the same time, markers (black circles) of a three-dimensional motion analyzer were mounted on the back surface of the subject. The markers were attached to positions corresponding to the position of the bones in relation to the posture of the subject in the sitting posture like in FIGS. 1 and 2. The markers were attached to seven points corresponding to the second cervical spine C2, the seventh cervical spine C7, the third thoracic spine T3, the eighth thoracic spine T8, the twelfth thoracic spine T12, the third lumbar spine L3, the sacrum S, additional two points front and rear sandwiching the measuring terminal 3, and one point on the operating screen 2a of the notebook PC.

The subject gradually moved away from the operating screen 2a from the initial posture (FIG. 6A) that leans forward to approach the operating screen 2a, moving the head and the neck upward and downward in harmony with a point that moves upward and downward on the operating screen until the subject comes to be in the front posture (FIG. 6B). During this period, the angles of given parts constituting the spinal alignment of the subject, the viewing distance d, and the slope angle $\theta_S$ were measured over time.

Figure 7:
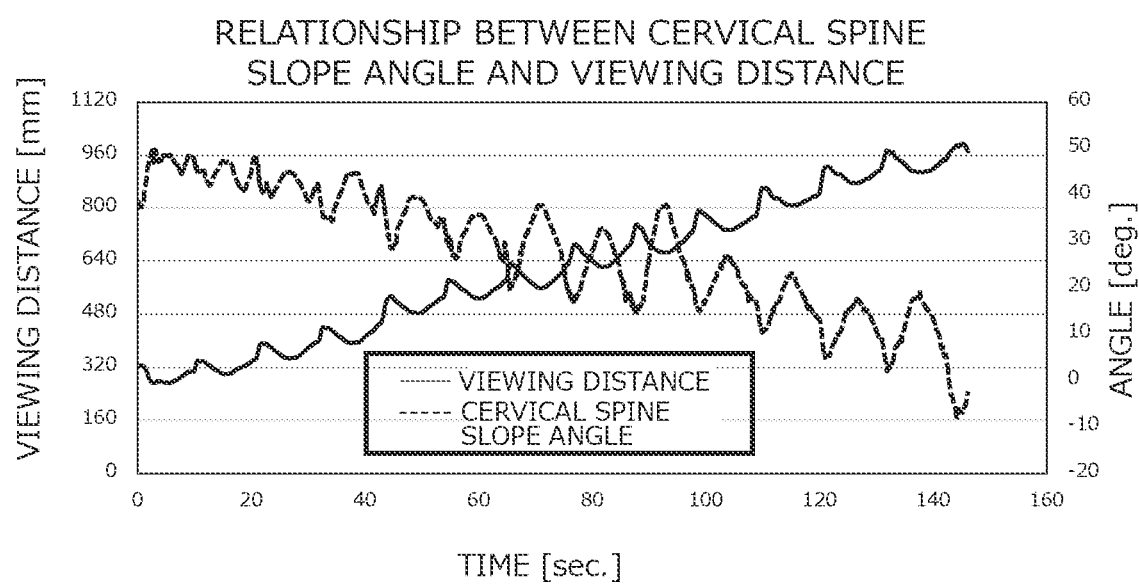
FIG. 7 is a diagram illustrating a correlation between a cervical spine slope angle and a viewing distance.
Figure 8:
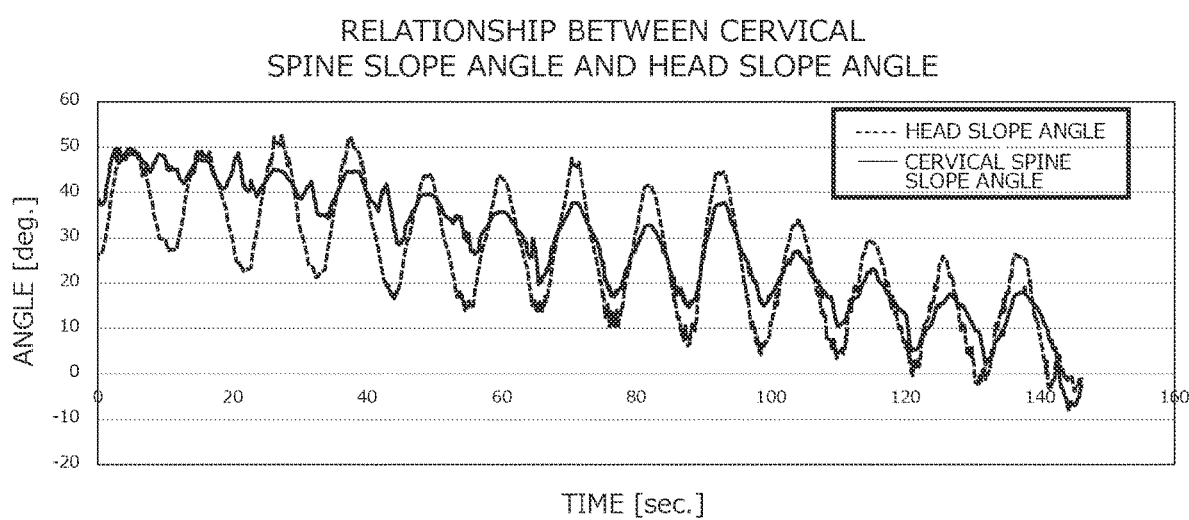
FIG. 8 is a diagram illustrating a correlation between the cervical spine slope angle and a head slope angle.

The result of the experiment showed correlations among all angles of the parts constituting the spinal alignment, the viewing distance d, and the slope angle $\theta_S$. As an example, FIG. 7 shows the correlation between the cervical spine slope angle and the viewing distance, and FIG. 8 shows the correlation between the cervical spine slope angle and the head slope angle. For the C2-C7 vertical angle (cervical spine slope angle), a strong negative correlation was observed between the C2-C7 vertical angle and the viewing distance d, and a strong positive correlation was observed between the C2-C7 vertical angle and the slope angle $\theta_S$ (see FIGS. 7 and 8).

From the above correlations, the angles $Y_1$ to $Y_5$ (hereinafter, also referred to as an estimated pseudo-angles) formed by given parts composing the spinal alignment can be calculated by a multiple regression analysis using data obtained from the measuring terminal 3 and the regression coefficients $A_1$ to $A_4$ and intercept (coefficient) $A_5$ obtained using the measurement results of the actual angles $Y_1$ to $Y_5$ obtained from the three-dimensional motion analyzer. The regression analysis may be n-th order (n is a natural number), preferably in the second order or less.

Assuming that the estimated pseudo-angles $Y_1$ to $Y_5$ are targets to be estimated (object variable $Y_m$) and the elements for varying the estimated pseudo-angle $Y_1$ to $Y_5$ are the slope angle $\theta_S$ (explanatory variable $X_1$) of the head and the viewing distance d (explanatory variable $X_2$) measured by the measuring terminal 3, these relationships are expressed by, for example, the following linear approximation expression.

$$Y_m = A_1 X_1 + A_2 X_2 + A_3 X_1^2 + A_4 X_2^2 + A_5 \qquad \text{[Expression 1]}$$

The expression 1 is a relational expression (multiple regression expression, model expression) of multiple regression analysis having multiple explanatory variables. The symbols $A_1$ to $A_4$ represent regression coefficients, and $A_5$ represents an intercept.

The symbol $Y_m$ is the angle (estimated pseudo-angle) formed by given parts constituting the spinal alignment, and m=1 to 5. Since the markers are attached to seven places corresponding to the second cervical spine C2, the seventh cervical spine C7, the third thoracic spine T3, the eighth thoracic spine T8, the twelfth thoracic spine T12, the third lumbar spine L3, and the sacrum S, the estimated pseudo-angles $Y_1$ to $Y_5$ here are pseudo values obtained by estimating the angles of the cervical forward slope angle, T1 slope, the upper thoracic kyphosis angle, the thoracic kyphosis angle, and the lumbar lordosis angle, which are significant in posture. The units for $Y_m$ and $X_1$ are [degrees] and the unit for $X_2$ is [mm]. Incidentally, the $Y_m$ to be obtained is not limited to the above angle, but may be an angle at a different location depending on the purpose, or more or less angles may be obtained.

The coefficient $A_1$ is the coefficient of the term of the slope angle $\theta_S$ of the head, and the coefficient $A_3$ is the coefficient of the term of the square of the slope angle $\theta_S$ of the head. The coefficient $A_2$ is the coefficient of the term of the viewing distance d, and the coefficient $A_4$ is the coefficient of the term of the square of the viewing distance d. The coefficient $A_5$ is an intercept.

The coefficients $A_1$ to $A_5$ are set differently for each user. In other words, the coefficients $A_1$ to $A_5$ are values corresponding to the attribute of a user. Examples of the attribute of the user include, for example, parameters such as age, gender, height, weight, and body shape.

The coefficients $A_1$ to $A_4$ are coefficients calculated from the correlation among the actual spinal alignment calculated by a three-dimensional motion analyzer, the slope angle $\theta_S$ of the head, and the viewing distance d of given subjects, measuring subjects, or users. The coefficient $A_5$ is the coefficient calculated in the process of calculating the coefficients $A_1$ to $A_4$. The manner of calculating the coefficient $A_1$ to $A_5$ will be described below.

Further, the coefficients $A_1$ to $A_5$ of Expression 1 are set to values corresponding to the angles formed by given parts constituting the spinal alignment. In other words, the values of the coefficients $A_1$ to $A_5$ vary with the values of the angles $Y_1$ to $Y_5$. Accordingly, the estimator 12 calculates $Y_m$ by substituting the viewing distance d and the slope angle $\theta_S$ into Expression 1 in which the coefficients $A_1$ to $A_5$ according to the attribute of the user and the $Y_m$ to be calculated are set.

When obtaining the viewing distance d and the slope angle $\theta_S$, the estimator 12 refers to the information stored in the storing device 10c and extracts the coefficients $A_1$ to $A_5$. FIG. 9 is a table showing an example of a result including the coefficients $A_1$ to $A_5$ calculated using a multiple regression analysis from values of the viewing distance d and the angle $\theta_S$ of the head of the user measured with the measuring terminal 3 of the present disclosure, and an actual measured values $Y_1$ to $Y_5$ with the three-dimensional motion analyzer. The table of the result of the multiple regression analysis is a table showing coefficients and the intercept necessary for calculating the pseudo-estimated angles.

(Table of Results of Multiple Regression Analysis)

As shown in FIG. 9, the table of result of multiple regression analysis may include fields of, for example, "intercept $A_5$", "coefficient $A_1$ of the term of the head slope angle $\theta_S$", "coefficient $A_2$ of the term of the viewing distance d", "coefficient $A_3$ of the term of the square of the head slope angle $\theta_S$", and "coefficient $A_4$ of the term of square of viewing distance d", and optionally "multiple correlation coefficient R" and "multiple coefficient $R_2$ of determination" on the vertical axis. Further, the table may include the fields of "C2-C7 vertical angle", "T1 slope", "C7-T3-T8", "T3-T8-T12", and "T12-L3-S" respectively indicating $Y_1$ to $Y_5$ on the horizontal axis.

(Calculation of the Coefficients $A_1$ to $A_5$)

From the result of an experiment, it was found that all the angles of the parts constituting the spinal alignment, the viewing distance d, and the slope angle $\theta_S$ are expressed by the expression of the regression analysis of Expression 1. Therefore, the coefficients $A_1$ to $A_5$ were obtained by substituting, in Expression 1, the data measured by the measuring terminal 3 into $X_1$ and $X_2$ and the values measured by using a three-dimensional motion analyzer at the same time as when measured by the measuring terminal 3 into the $Y_m$. The values of the coefficients $A_1$ to $A_5$ can be said to be calculated by statistically fitting the results of several measurements to an approximate expression.

In relation to regression analysis, a first-order regression analysis (first-order linear approximation) resulted in large dispersion, whereas a second-order regression analysis (second-order linear approximation) resulted in less dispersion.

As shown in the field of "multiple correlation coefficient R" in FIG. 9, the values of the correlation coefficients by the method are in the range of 0.735 to 0.972, and from this result, it can be seen that $Y_m$, which are calculated by substituting the viewing distance d and the slope angle $\theta_S$ into $X_1$ and $X_2$ of Expression 1 in which the coefficients $A_1$ to $A_5$ set according to $Y_m$, are estimated with very high accuracy.

The estimator 12 compares the calculated value of $Y_1$ to $Y_5$ with values within respective given ranges. Examples of the values of the given ranges are angles within ranges of a reference posture, that is, angles within ranges of a correct posture which is ideal from a medical point of view in which a load is not applied to the parts constituting the spinal alignment in view of the shape of the spine. As a result of the comparison, when the values of $Y_1$ to $Y_5$ are not within respective given ranges, the evaluation information indicating a bad posture is transmitted to the notifier 13. In this case, information indicating which part of the spine is particularly loaded may be transmitted.

The estimator 12 may evaluate (judge) the bad posture according to the time or frequency when the values of the $Y_1$ to $Y_5$ are not within the given ranges. For example, the estimator 12 may evaluate the bad posture based on not only the measurement time (instant) of the viewing distance d and the slope angle $\theta_S$ but also a value obtained by accumulating the time period or the frequency in which the values of the $Y_1$ to $Y_5$ are not in the given ranges. For example, if the time during which the values of the $Y_1$ to $Y_5$ are not within given ranges occupies 5% per hour or is counted 10 times in one day, the posture may be evaluated (determined) by comparing the ratio (value) with a given threshold. Alternatively, a value related to abnormality may be calculated through machine learning on the values of $Y_1$ to $Y_5$ when the user answers having uncomfortability, pain, or feeling abnormality in the spine as a result of responding to a questionnaire or the like, and the posture may be evaluated by using the calculated value.

The estimator 12 prepares the coefficients $A_1$ to $A_5$ obtained by using the spinal alignment estimating system 100 and the three-dimensional motion analyzer in a table form and stores the table in the storing device 10c (which will be described below with reference to FIG. 11).

This table may be an individual table unique to an individual user of the measurement subject, or may be a table generated by machine-learning on a huge amount of measured data and classifying them according to the attribute of the measurement subject. The table is selected and used by a user that is to use the spinal alignment estimating system 100 according to his/her own attribute. The attribute include gender, age, body shape, and others. In the table, the coefficients $A_1$ to $A_5$ are determined according to the combinations of gender, age, and body shape, and the user can easily estimate his/her spinal alignment with the spinal alignment estimating system 100 by selecting his/her own attribute. For example, the coefficients $A_1$ to $A_5$ of FIG. 9 correspond to "gender: male, age: twenties, body type: slender", are formed into a table to be the values of the attribute in question, and stored in the storing device 10c. Alternatively, the coefficients $A_1$ to $A_5$ may be stored in an external server or the like.

In addition, the tables may have optimum coefficients $A_1$ to $A_5$ depending not only on the attribute but also on the state of the user. The state is a sitting posture in a chair, a sitting posture on the heels (seiza), a standing posture, a supine posture, and the like. The user can estimate the spinal alignment in any state by setting the state at the time of use in the spinal alignment estimating system 100.

[1-5] Example of Operation

Figure 10:
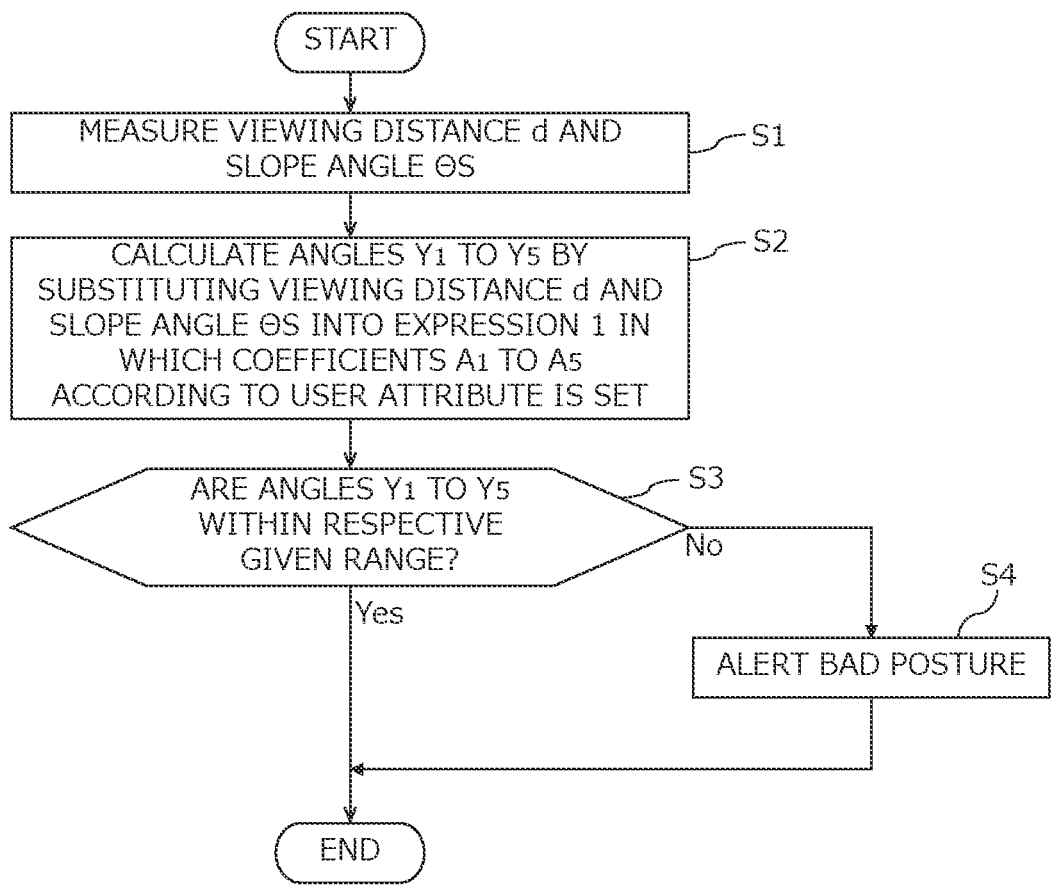
FIG. 10 is a flow diagram illustrating an example of operating of the system for estimating a spinal alignment of the one embodiment.

Hereinafter, an example of operating of the spinal alignment estimating system 100 will be described. FIG. 10 is a flow diagram illustrating an example of the operation of the spinal alignment estimating system 100 of the one embodiment.

The first measuring unit 31 of the measuring terminal 3 measures the viewing distance d between the operating screen 2a and the user, and the second measuring unit 32 of the measuring terminal 3 measures the slope angle $\theta_S$ of the head of the user facing the operating screen 2a of the operating terminal 2 (Step S1).

The obtaining unit 11 of the spinal alignment estimating apparatus 1 obtains the viewing distance d and the slope angle $\theta_S$ from the measuring terminal 3. The estimator 12 calculates the angles $Y_1$ to $Y_5$ of given parts of the user's spine by substituting the viewing distance d and the slope angle $\theta_S$ into Expression 1 in which the coefficients $A_1$ to $A_5$ corresponding to the attribute of the user are set (Step S2). Furthermore, the estimator 12, at the time of measurement, determines whether or not the values of the angles $Y_1$ to $Y_5$ in a continuous constant time (period) are within respective given ranges (Step S3).

If the values of the angles $Y_1$ to $Y_5$ are determined not to be within the given ranges (or if the time period or frequency at which the angles $Y_1$ to $Y_5$ are not within given ranges exceeds a given threshold), the notifier 13 of the spinal alignment estimating device 1 notifies the operating terminal 2 that the posture estimated from the user's spinal alignment is bad, and causes the operating terminal 2 to display an alert of the bad posture (Step S4). Then, the process ends.

On the other hand, in Step S3, if the values of the angles $Y_1$ to $Y_5$ are determined to be within the given ranges, the process ends without displaying an alert or the like in the operating terminal 2.

[1-6] Effect

As described above, the spinal alignment estimating apparatus 1, the system for estimating a spinal alignment 100, the method for estimating a spinal alignment, the program for estimating a spinal alignment, and the computer-readable recording medium having stored therein a program for estimating a spinal alignment bring the following effects, for example.

The spinal alignment estimating apparatus 1 estimates the spinal alignment based on the viewing distance d to the user in front of the operating screen 2a of the operating terminal 2 and the slope angle $\theta_S$ of the head of the user facing the operating screen 2a. This makes it possible to dynamically estimate the spinal alignment over time from two pieces of information without using a large-scale device.

The spinal alignment estimating apparatus 1 estimates the spinal alignment of the user by calculating the angles $Y_1$ to $Y_5$ formed by given parts constituting the spinal alignment. This allows accurate estimation of the spinal alignment of the user in the sitting posture.

On the basis of $A_1$ to $A_5$ calculated through the experiment shown in FIG. 6A and FIG. 6B, the spinal alignment estimating apparatus 1 calculates the angles $Y_1$ to $Y_5$ formed by given parts of the spinal alignment of the user. This makes it possible to obtain a value very close (highly correlated with) to the data value obtained by the three-dimensional motion analyzer. Therefore, the spinal alignment of the user can be estimated more accurately.

The spinal alignment estimating apparatus 1 notifies the user of an abnormal posture when the angle $Y_1$ to $Y_5$ formed by given parts constituting the spinal alignment calculated by the estimator 12 are not within given ranges. In response, the user can voluntarily correct his/her posture.

Figure 11:
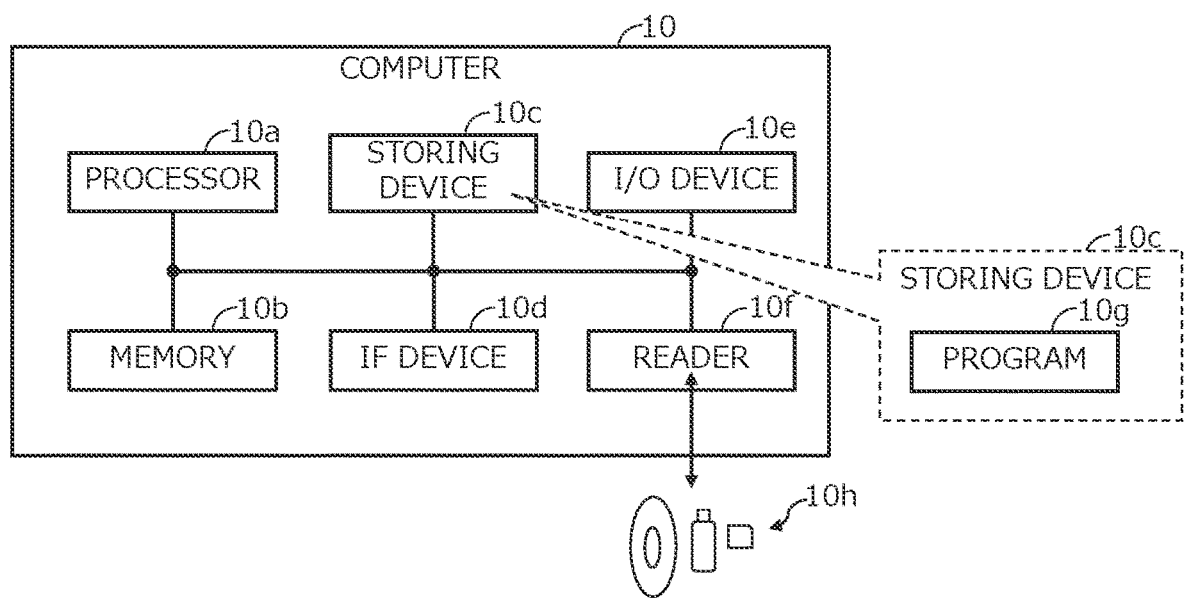
FIG. 11 is a block diagram illustrating an example of a hardware configuration of a computer of the one embodiment.

[1-7] Example of Hardware Configuration of Spinal Alignment Estimating Apparatus FIG. 11 is a block diagram illustrating an example of a hardware configuration of a computer that achieves the function of the spinal alignment estimating apparatus 1. When multiple computers are used as the hardware resources that achieve the function of the spinal alignment estimating apparatus 1, each computer may have the hardware configuration illustrated in FIG. 11.

As illustrated in FIG. 11, the computer 10 may exemplarily include a processor 10a, a memory 10b, a storing device 10c, an IF (Interface) device 10d, an IO (Input/Output) device 10e, and a reader 10f as the HW configuration.

The processor 10a is an example of an arithmetic processing apparatus that performs various controls and arithmetic operations. The processor 10a may be communicably connected to the blocks in the computer 10 to each other via a bus 10i. The processor 10a may be a multiprocessor including multiple processors, a multi-core processor including multiple processor cores, or a configuration including multiple multi-core processors.

An example of the processor 10a is an Integrated Circuit (IC) such as a Central Processing Unit (CPU), a Micro Processing Unit (MPU), a Graphics Processing Unit (GPU), an Accelerated Processing Unit (APU), a Digital Signal Processor (DSP), an Application Specific IC (ASIC), and a Field-Programmable Gate Array (FPGA). Alternatively, the processor 10a may be a combination of two or more ICs exemplified as the above.

The memory 10b is an example of a HW device that stores information such as various data pieces and a program. An example of the memory 10b includes one or both of a volatile memory such as the Dynamic Random Access Memory (DRAM) and a non-volatile memory such as the Persistent Memory (PM).

The storing device 10c is an example of a HW device that stores information such as various data pieces and programs. Examples of the storing device 10c is various storing devices exemplified by a magnetic disk device such as a Hard Disk Drive (HDD), a semiconductor drive device such as an Solid State Drive (SSD), and a non-volatile memory. Examples of a non-volatile memory are a flash memory, a Storage Class Memory (SCM), and a Read Only Memory (ROM).

In addition, the storing device 10c may store a program 10g (program for estimating a spinal alignment) that implements all or part of the functions of the computer 10. For example, the processor 10a of the spinal alignment estimating apparatus 1 can implement the function of the spinal alignment estimating apparatus 1 illustrated in FIG. 3 by, for example, expanding the program 10g stored in the storing device 10c onto the memory 10b and executing the expanded program.

The IF device 10d is an example of a communication IF that controls connection to and communication with a network. For example, the IF device 10d may include an adaptor compatible with a Local Area Network (LAN) such as Ethernet (registered trademark) and an optical communication such as Fibre Channel (FC). The adaptor may be compatible with one of or both of wired and wireless communication schemes. For example, the spinal alignment estimating apparatus 1 may be communicably connected with the operating terminal 2 or the terminal 3 via the IF device 10d. Further, the program 10g (program for estimating a spinal alignment) may be downloaded from a network to a computer 10 through the communication IF and then stored into the storing device 10c, for example.

The I/O device 10e may include one of or both of an input device and an output device. Examples of the input device are a keyboard, a mouse, and a touch screen. Examples of the output device are a monitor, a projector, a printer, and an audio device.

The reader 10f is an example of a reader that reads information of data and a program recorded on a recording medium 10h. The reader 10f may include a connecting terminal or a device to which the recording medium 10h can be connected or inserted. Examples of the reader 10f include an adapter conforming to, for example, Universal Serial Bus (USB), a drive apparatus that accesses a recording disk, and a card reader that accesses a flash memory such as an SD card. The program 10g (e.g., a program for estimating a spinal alignment) may be stored in the recording medium 10h, and the reader 10f may read the program 10g from the recording medium 10h and store the read program 10g (program for estimating a spinal alignment) into the storing device 10c.

An example of the recording medium 10h is a non-transitory computer-readable recording medium such as a magnetic/optical disk, and a flash memory. Examples of the magnetic/optical disk include a flexible disk, a Compact Disc (CD), a Digital Versatile Disc (DVD), a Blu-ray disk, and a Holographic Versatile Disc (HVD). Examples of the flash memory include a semiconductor memory such as a USB memory and an SD card.

The HW configuration of the computer 10 described above is merely illustrative. Accordingly, the computer 10 may appropriately undergo increase or decrease of HW (e.g., addition or deletion of arbitrary blocks), division, integration in an arbitrary combination, and addition or deletion of the bus. For example, at least one of the I/O device 10e and the reader 10f may be omitted in the spinal alignment estimating apparatus 1.

The operating terminal 2, which is an example of the information processing terminal, may be achieved by the same HW configuration as that of the computer 10 described above.

For example, the processor 10a of the operating terminal 2 can achieve the function as the operating terminal 2 shown in FIG. 3 by expanding a program 10g (e.g., program for estimating a spinal alignment) stored in the storing device 10c on the memory 10b and executing the expanded program 10g.

The operating terminal 2 shown in FIG. 3 may include an input device which is an example of the I/O unit 10e. Further, the processor 10a of the operating terminal 2 may transmit information (e.g., user attribute) input by the user through the input device to the spinal alignment estimating apparatus 1 via the IF device 10d.

[2] Miscellaneous

The technique according to the above-described embodiment can be implemented after being changed or modified as follows.

In the above embodiment, the measurement of the viewing distance d is accomplished by the measuring terminal 3. Alternatively, if a camera is built in the operating terminal 2, the distance d may be measured with the camera. In addition, although the viewing distance d and the slope angle $\theta_S$ are measured by different apparatuses, these values may be measured using only a three-axis acceleration sensor, for example.

The spinal alignment estimating apparatus 1 may be incorporated in the operating terminal 2. In this alternative, the notification by the notifier 13 may be displayed on the display unit 21.

The spinal alignment estimating apparatus 1 may be integrated with the measuring terminal 3. The display of the abnormality of the posture to the user may be performed by any of the spinal alignment estimating apparatus 1, the operating terminal 2, and the measuring terminal 3. The alerting method may be any method as long as it is detected by a human in addition to method utilizing the visual sense and the auditory sense.

The coefficients $A_1$ to $A_5$ are only coefficients related to the slope angle $\theta_S$ of the head or the viewing distance, and are not limited to the values obtained in the experiment calculated by the three-dimensional motion analyzer described in the above embodiment. Alternatively, the coefficients $A_1$ to $A_5$ may be calculated by capturing multiple images of user's postures on the operating screen 2a, sending the images to a given institution or agency where a three-dimensional operation analysis carries out.

The viewing distance d, the slope angle $\theta_S$, the value of the coefficients $A_1$ to $A_5$, and the values of the angles $Y_1$ to $Y_5$ may be corrected according to various conditions such as measurement conditions.

The values of the angles $Y_1$ to $Y_5$ calculated by substituting multiple patterns of the viewing distance d, the slope angle $\theta_S$, and the coefficients $A_1$ to $A_5$ for each attribute of a user into Expression 1 may be stored as a data file in the storing device 10c in advance. In this case, the estimator 12 may refer to the data file stored in the storing device 10c on the basis of the obtained viewing distance d and the slope angle $\theta_S$ and extract the values of the angles $Y_1$ to $Y_5$ calculated by using the coefficients $A_1$ to $A_5$ corresponding to the attribute of the user.

The coefficients $A_1$ to $A_5$ may be set according to the viewing target or the relationship between the viewing target and the user. For example, if the viewing target is a book or a portable device, the relationship between the viewing target and the head of the user is determined by the position of the hand with the viewing target, so that the coefficients $A_1$ to $A_5$ may be set according to the situation. Further, in cases where the viewing target is a visual display terminal exemplified by a fixed computer display and the user is seated in front of the viewing target, the positional relationship between the user and the viewing target does not largely fluctuate, and therefore the distance between the user and the viewing target is substantially constant. On the other hand, the distance to the viewing target changes with the position where the user is sitting in some circumstances. To deal with such circumstances, the coefficients $A_1$ to $A_5$ may be set according to the status (positional relationship) between the user and the viewing target.

In the claims, the indefinite article "a" or "an" does not exclude a plurality.

All examples and conditional language recited herein are intended for the pedagogical purposes of aiding the reader in understanding the disclosure and the concepts contributed by the inventor to further the art, and are not to be construed limitations to such specifically recited examples and conditions, nor does the organization of such examples in the specification relate to a showing of the superiority and inferiority of the disclosure. Although one or more embodiments of the present disclosures have been described in detail, it should be understood that the various changes, substitutions, and alterations could be made hereto without departing from the spirit and scope of the disclosure.

What is claimed is:

1. A spinal alignment estimating system comprising an operating terminal, a measuring terminal, and a spinal alignment estimating apparatus, wherein
the operating terminal comprises a screen that displays information of a viewing target,
the measuring terminal comprises:
a position measuring device including:
at least one of an optical distance measuring sensor, a radio distance measuring sensor, and an ultrasonic distance measuring sensor, and
an angle measuring device including:
at least one of an acceleration sensor, an inertial sensor, and a slope sensor,
the position measuring device measures a distance between the operating terminal and the measuring terminal, and the angle measuring device obtains an angle of a head of a user,
the spinal alignment estimating apparatus comprises:
a memory; and
processor circuitry coupled to the memory, wirelessly or wiredly connected to the measuring terminal and the operating terminal, the processor circuitry being configured to:
calculate, based on a position of the head of the user measured by the position measuring device and the angle of the head of the user obtained by the angle measuring device, one or more estimated pseudo angles formed by given parts constituting a spinal alignment including a cervical spine, a thoracic spine, a lumbar spine, a sacrum, and a coccyx.

2. The spinal alignment estimating system according to claim 1, wherein the processor circuitry is configured to calculate the one or more estimated pseudo angles formed by the given parts by using the position of the head of the user, the angle of the head of the user, and a coefficient according to an attribute of the user.

3. The spinal alignment estimating system according to claim 1, the processor circuitry the processor circuitry is further configured to notify, when the one or more estimated pseudo angles formed by the given parts calculated by the processor circuitry is outside a given range, the user of abnormality of a posture.

4. A computer-implemented method for estimating a spinal alignment carried out by a spinal alignment estimating system comprising an operating terminal, a measuring terminal, and a spinal alignment estimating apparatus, the method comprising:
displaying a viewing target on a screen of the operating terminal;
measuring a distance between the operating terminal and the measuring terminal with a positioning measuring device of the measuring terminal, and obtaining an angle of a head of a user with an angle measuring device of the measuring terminal; and
at processor circuitry of spinal alignment estimating system spinal alignment estimating system,
calculating, based on the position of the head of the user obtained by a position measuring device and the angle of the head of the user obtained by the angle measuring device of the measuring terminal, one or more of estimated pseudo angles formed by given parts constituting the spinal alignment including a cervical spine, a thoracic spine, a lumbar spine, a sacrum, and a coccyx.

5. The method according to claim 4, wherein the method calculates the one or more of the estimated pseudo angles formed by the given parts based on the position of the head of the user, the angle of the head of the user, and a coefficient according to an attribute of the user.

6. The method according to claim 4, further comprising:
at processor circuitry processor circuitry of spinal alignment estimating system spinal alignment estimating system,
notifying, when the one or more of the estimated pseudo angles formed by the given parts is outside a given range, the user of abnormality of a posture.

7. A non-transitory computer-readable recording medium being used by a spinal alignment estimating system comprising an operating terminal, a measuring terminal, and a spinal alignment estimating apparatus and having stored therein a spinal alignment estimating program that causes the computer to execute a method, the method comprising:
displaying a viewing target on a screen of the operating terminal;
measuring a distance between the operating terminal and the measuring terminal with a positioning measuring device of the measuring terminal, and obtaining an angle of a head of a user with an angle measuring device of the measuring terminal; and
at processor circuitry of spinal alignment estimating system spinal alignment estimating system,
calculating, based on the position of the head of the user obtained by a position measuring device and the angle of the head of the user obtained by the angle measuring device, one or more estimated pseudo angles formed by given parts constituting a spinal alignment including a cervical spine, a thoracic spine, a lumbar spine, a sacrum, and a coccyx.

8. The non-transitory computer-readable recording medium according to claim 7, wherein the method calculates the one or more estimated pseudo angles formed by the given parts by using the position of the head of the user, the angle of the head of the user, and a coefficient according to an attribute of the user.

9. The non-transitory computer-readable recording medium according to claim 7, the method further comprising notifying, when the one or more of the estimated pseudo angles formed by the given parts is outside a given range, the user of abnormality of a posture.

* * * * *